(12) United States Patent
Kelly, Sr.

(10) Patent No.: US 7,347,691 B1
(45) Date of Patent: Mar. 25, 2008

(54) PROTECTIVE SLEEVE FOR SALIVA EJECTOR

(75) Inventor: Daniel E. Kelly, Sr., Coral Springs, FL (US)

(73) Assignee: Ines Collia Kelly, Coral Springs, FL (US)

( * ) Notice: Subject to any disclaimer, the term of this patent is extended or adjusted under 35 U.S.C. 154(b) by 0 days.

(21) Appl. No.: 11/645,682

(22) Filed: Dec. 27, 2006

(51) Int. Cl.
*A61C 17/14* (2006.01)

(52) U.S. Cl. ...................................... 433/91

(58) Field of Classification Search ............ 433/91–96, 433/147; 604/128–129; 601/139
See application file for complete search history.

(56) References Cited

U.S. PATENT DOCUMENTS

| | | | |
|---|---|---|---|
| 2,504,557 A | 4/1950 | Lumian | |
| 2,595,666 A | 5/1952 | Hutson | |
| 2,637,106 A * | 5/1953 | Otis | 433/91 |
| 2,644,234 A | 7/1953 | Scott | |
| 2,979,056 A * | 4/1961 | Wiseman | 604/275 |
| 3,753,292 A * | 8/1973 | Hutson | 433/96 |
| 3,758,950 A * | 9/1973 | Krouzian | 433/91 |
| 4,158,916 A | 6/1979 | Adler | |
| 4,233,025 A | 11/1980 | Larson et al. | |
| D258,531 S | 3/1981 | Orsing | |
| 4,653,480 A * | 3/1987 | Rabinowitz | 601/141 |
| 5,094,616 A | 3/1992 | Levenson | |
| 5,119,803 A * | 6/1992 | Fishman | 601/139 |
| 5,151,094 A | 9/1992 | Hanifl | |
| D357,064 S | 4/1995 | Bartlett et al. | |
| 5,690,487 A | 11/1997 | Whitehouse et al. | |
| 5,975,897 A | 11/1999 | Propp et al. | |
| 6,022,326 A | 2/2000 | Tatum et al. | |
| 6,068,476 A | 5/2000 | Point | |
| 6,068,477 A | 5/2000 | Mahlmann | |
| 2006/0024641 A1 | 2/2006 | Mahlmann | |

FOREIGN PATENT DOCUMENTS

DE  3726349  2/1989

OTHER PUBLICATIONS

Website http://www.kerrtotalcare.com/products/pinnacleSyringeSleeve/index.cfm, thin plastic sleeve loosely covering handles of dental appliances, one sheet printed from the Internet on Apr. 28, 2006.

* cited by examiner

*Primary Examiner*—John J Wilson
(74) *Attorney, Agent, or Firm*—Richard C. Litman

(57) ABSTRACT

The protective sleeve for a saliva ejector is formed of a soft, porous plastic material for installation upon the end of a conventional ejector tube to protect the soft tissues within the mouth of a dental patient during dental work. The device has a generally cylindrical external configuration with a frustoconical installation passage formed concentrically therein. The installation passage has a relatively wide mouth and narrower neck portion within the intermediate portion of the sleeve. The installation passage widens within the distal end portion of the device, to provide clearance for the larger diameter head of the ejector tube. This results in a necked-down portion in the intermediate portion of the device. The distal end of the device is closed, with a larger diameter bulbed external portion providing further cushioning.

4 Claims, 5 Drawing Sheets

PROTECTIVE SLEEVE FOR SALIVA EJECTOR

BACKGROUND OF THE INVENTION

1. Field of the Invention

The present invention relates generally to medical appliances for use in the field of dentistry and the like. More specifically, the present invention comprises relates to a protective sleeve for a saliva ejector (suction tube).

2. Description of the Related Art

The removal of excessive saliva and fluids from the mouth of a patient is a standard procedure for persons undergoing dental work. For years, this has been accomplished by means of powered suction devices connected to saliva ejector tubes inserted in the mouth of the patient. The ejector tube(s) may be positioned in the mouth continuously or intermittently during the dental procedure.

In order to facilitate hygiene, the portion of the ejector tube apparatus that is inserted in the mouth of the patient generally comprises a disposable, single use plastic tube. Even though the device is formed of plastic, it is nevertheless relatively hard and uncomfortable in the mouth of the patient. The need to optimally position the open distal end of the tube, and the relative hardness and rigidity of the tube, can result in irritation and/or abrasion of the soft tissues in the mouth of the patient.

As a result, various soft pads have been developed in the past for placement over at least the open distal end of the ejector tube. However, most of these have proven unsatisfactory, at least to a certain extent. Most such devices essentially comprise a tube with a continually open passage extending from end to end. As such, the pad is prone to slipping along the length of the ejector tube, either toward or away from the open distal end of the tube, thus exposing the hard plastic of the distal end of the tube. This is particularly true when the assembly is exposed to saliva in the mouth of the patient, as saliva is a very effective lubricant.

When a pad or protective cushion slips from the distal end of the tube and becomes separated from the tube while in the mouth of the patient, the dentist or assistant must stop the work in progress, remove the ejector tube and the separated cushion or pad from the patient's mouth, reinstall the cushion on the end of the tube or install a new cushion thereon, and reposition the tube in the patient's mouth before continuing with the procedure. Obviously, this entails a considerable amount of time when the problem occurs even a few times during the course of a dental procedure.

The present inventor is aware of various devices relating to saliva ejector systems used in the dental field, in addition to the above noted technology. For example, German Patent No. 3,726,349, published on Feb. 16, 1989, describes (according to the drawings and English abstract) a pump apparatus and relatively small nozzle for cleaning the interperiodontal regions of the mouth.

Thus, a protective sleeve for a saliva ejector solving the aforementioned problems is desired.

SUMMARY OF THE INVENTION

The protective sleeve for a saliva ejector comprises various embodiments of a sleeve having an open end for installation over the ejector tube, and a closed opposite end completely enclosing the distal end of the tube. The device may be formed of any of a variety of soft, porous materials, e.g., open cell foam plastic material, etc. The material should be soft and porous so that fluids may pass through the wall of the device from its external surface to the internal cavity, to be drawn away by the ejector tube and pump assembly.

All of the various embodiments of the protective sleeve include an internal passage having a conical section with a relatively small internal diameter, which increases to a larger installation end diameter in order to facilitate the placement of the device over the end of an ejector tube or the like. The internal passage increases to a larger diameter within the distal portion of the device in order to fit around the larger diameter distal end of the conventional ejector tube. The external portion of the distal end of the device is preferably bulbed, i.e., provided with a larger diameter than the remainder of the device, in order to provide additional cushioning thickness over the end of the ejector tube.

These and other features of the present invention will become readily apparent upon further review of the following specification and drawings.

BRIEF DESCRIPTION OF THE DRAWINGS

FIG. 1 is an environmental, side elevation view of a protective sleeve for a saliva ejector according to the present invention, providing an exemplary showing of placement within the mouth of a dental patient or the like.

Similar reference characters denote corresponding features consistently throughout the attached drawings.

DETAILED DESCRIPTION OF THE PREFERRED EMBODIMENTS

The present invention comprises various embodiments of a disposable protective sleeve for a saliva ejector tube for use in dentistry and similar fields. The sleeve is specifically configured internally to secure positively to a conventional saliva ejector tube having a larger diameter distal end portion, the sleeve having a bulbed distal portion to provide greater cushioning over the distal end portion of the ejector tube.

Figure 1:
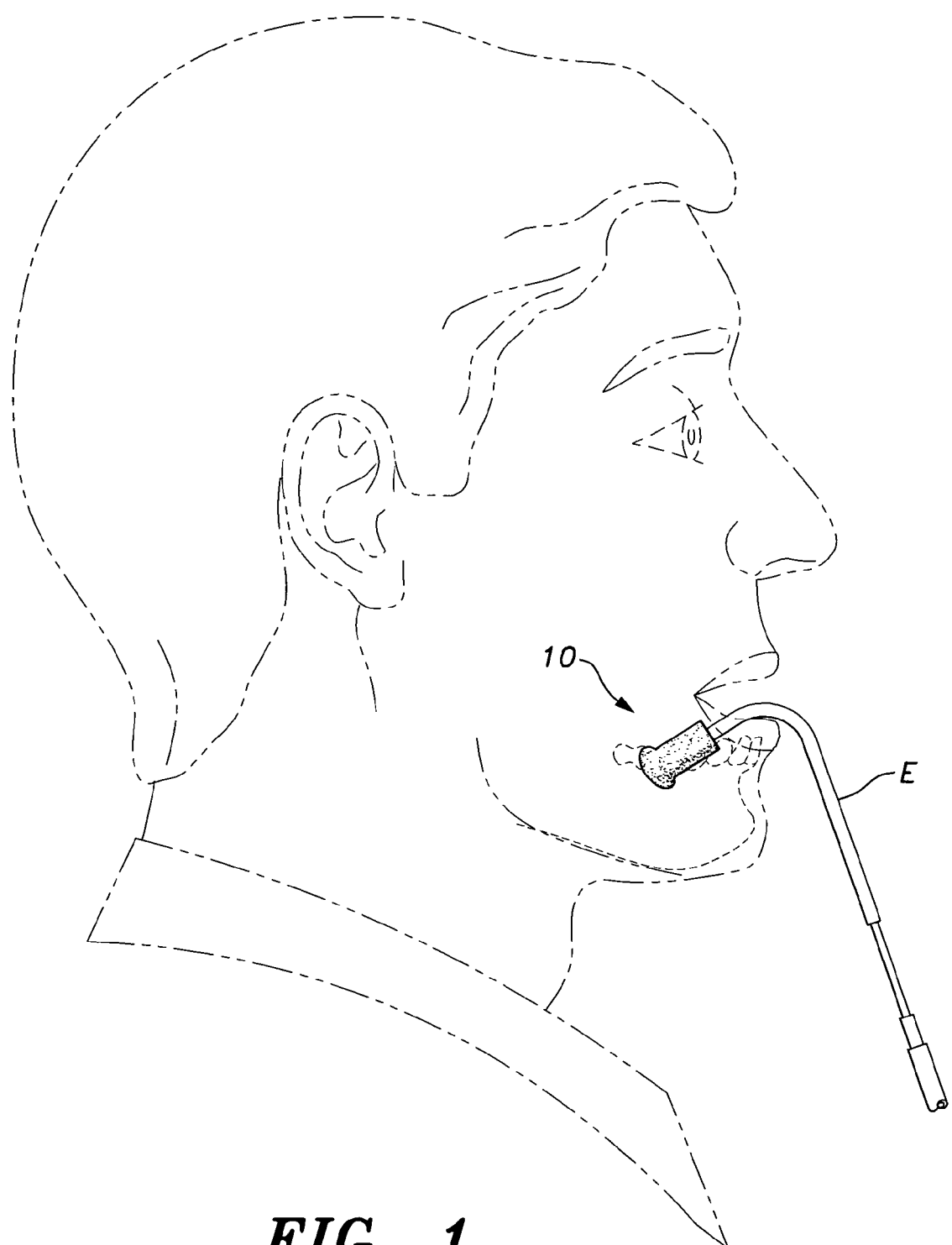

FIG. 1 of the drawings provides an environmental side elevation view of a first embodiment of the protective sleeve 10, with the sleeve 10 disposed on the distal end of a saliva ejector tube E. The sleeve 10 is formed of a soft, resilient, porous material, such as an open cell foam plastic or other material having similar suitable properties. Any material may be used that provides for: (a) passage of liquids therethrough, so the ejector tube may draw saliva and/or other liquids through the wall of the sleeve 10; and (b) cushioning between the soft tissues within the mouth of the patient and the relatively hard end of the ejector tube.

Figure 2:
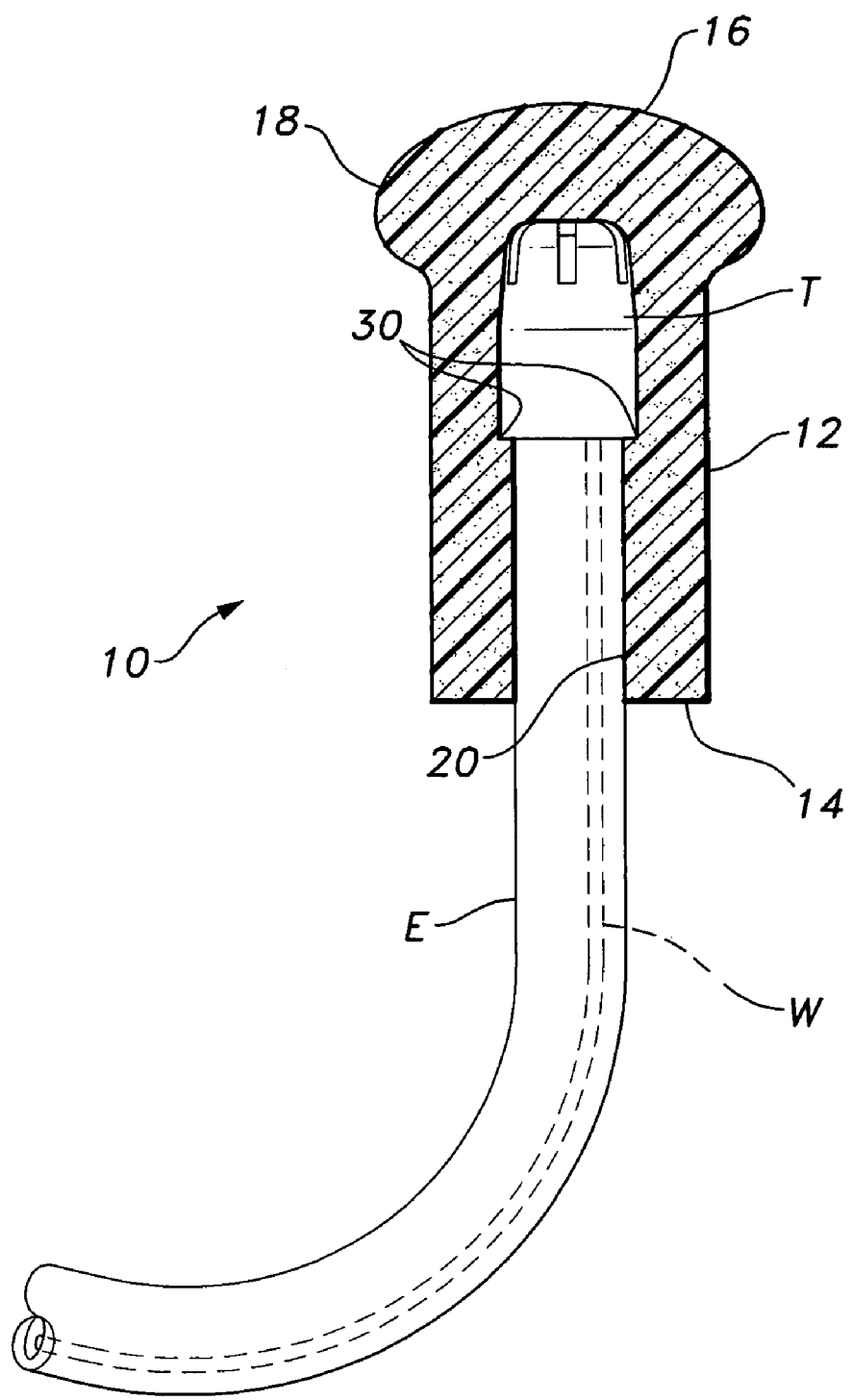
FIG. 2 is an environmental side elevation view in partial section of a protective sleeve for a saliva ejector according to the present invention, showing a first embodiment of the protective sleeve in section installed upon a conventional saliva ejector tube.
Figure 3:
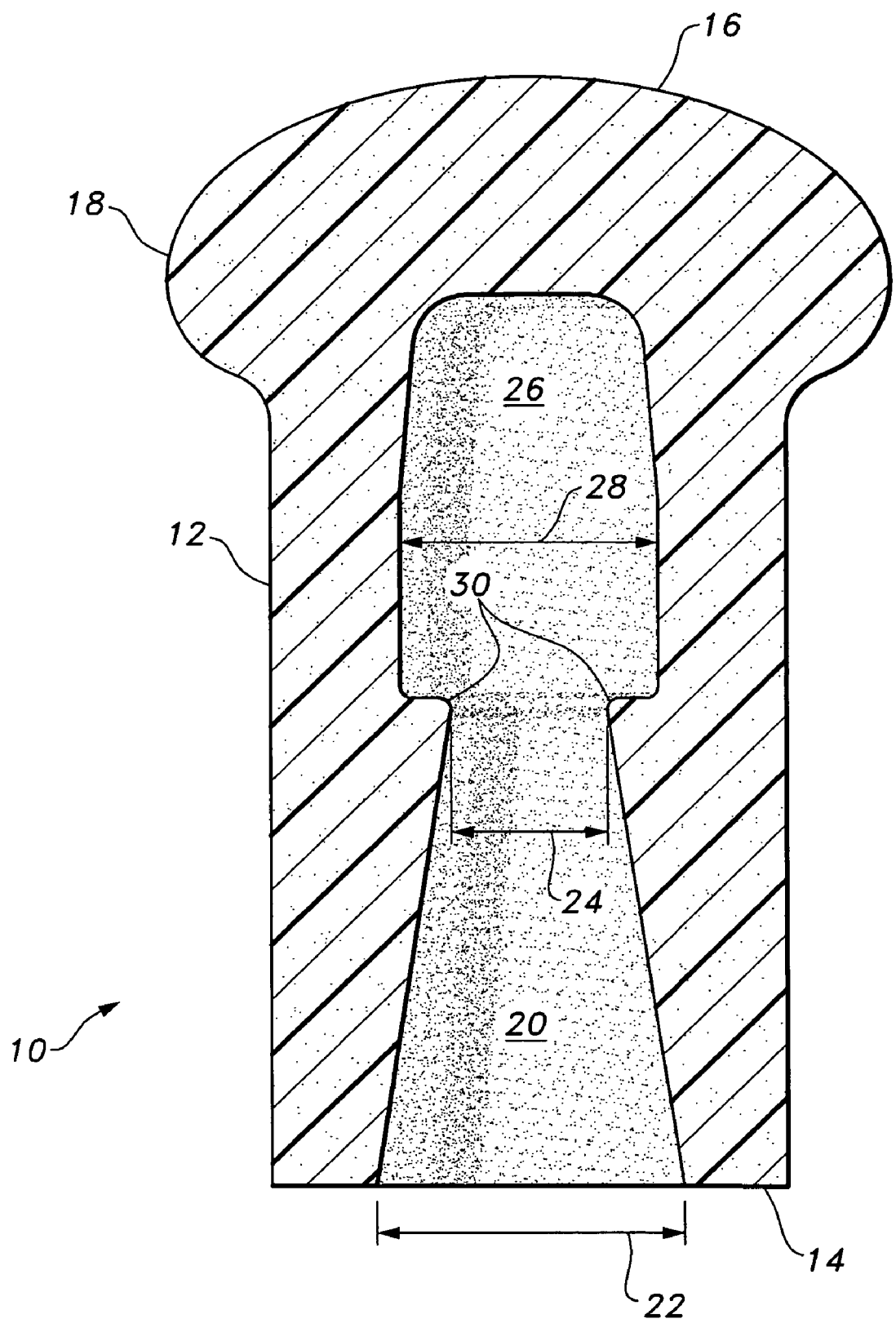
FIG. 3 is a substantially enlarged side elevation view of the protective sleeve of FIG. 2, showing further details of the internal configuration thereof.

FIGS. 2 and 3 illustrate further details of the protective sleeve 10, with FIG. 2 showing the sleeve 10 installed upon an ejector tube E and FIG. 3 showing the uninstalled sleeve 10. The sleeve 10 preferably has a body 12 with a generally cylindrical configuration, the body 12 having an open end 14 and an opposite closed end 16. The open end 14 is more clearly shown in FIGS. 2 and 3 of the drawings. The closed end 16 serves to prevent the sleeve 10 from sliding past the distal end portion of the ejector tube E, as the distal pickup end of the tube E and its surrounding sleeve are shifted in the patient's mouth. The closed end 16 of the body 12 preferably includes an externally bulbed portion 18 extending therefrom, with the bulbed portion having a larger diameter than the cylindrical body portion 12 to provide cushioning.

In FIG. 2, the protective sleeve 10 is shown in section, installed upon a conventional ejector tube E. The ejector tube E is formed of flexible plastic tubing, and may include an internal stiffening wire W to allow the tube to be bent to a desired shape and to hold that shape. The ejector tube E further includes a relatively larger diameter porous distal tip T through which saliva and/or other liquids may be drawn when the suction mechanism is in operation. The larger diameter of the distal tip T allows the protective sleeve 10 to grip the tube E below the tip T thereof, thereby providing positive elastic attachment of the sleeve 10 on the ejector tube E. It will be understood that the internal passage of the sleeve 10 shown in FIG. 2 is distended to fit closely about the ejector tube E, and thus the internal shape of the sleeve 10 in its relaxed condition is not shown in FIG. 2.

FIG. 3 provides an elevation view in section of the protective sleeve 10, illustrating further internal details thereof. The body 12 of the sleeve 10 defines a generally concentric ejector tube passage 20 therein, with the passage 20 having a relatively large diameter opening 22 at the open end 14 of the sleeve 10 and a relatively smaller diameter necked-down portion 24 disposed generally medially within the body 12. The internal diameter of the passage 20 tapers at a constant rate between the opening diameter 22 and neck diameter 24, thereby defining a frustoconical or truncated conical shape. The body 12 further defines a generally cylindrical cavity 26 disposed in the forward portion thereof, i.e., between the neck portion 24 of the passage 20 and the closed distal end 16 of the body 12. The cavity 26 has an intermediate diameter 28, i.e., a diameter smaller than the larger opening diameter 22 and greater than the smaller neck diameter 24 of the passage 20. Thus, the smaller diameter neck 24 of the passage 20 provides an annular body retaining element 30 when the sleeve 10 is installed upon an ejector tube E with the neck 24 of the sleeve positioned beyond the larger diameter distal tip portion T of the tube, with the body retaining element 30 and the resilient nature of the material providing positive retention of the sleeve 10 upon the end of the ejector tube E once installed thereon.

The protective sleeve 10 is installed upon the distal end of the ejector tube E generally as shown in FIG. 2 of the drawings, with the neck 24 and its annular retaining element 30 disposed behind the rearward portion of the larger diameter tip T to provide positive attachment of the sleeve 10 to the ejector tube E. The sleeve 10 is manufactured of economical materials, and, thus, may be installed upon the disposable ejector tube E at the time of manufacture and provided in combination therewith, if so desired. Alternatively, the sleeve 10 may be quickly and easily installed over the end of the ejector tube E in the dental office, with the relatively wide opening diameter 22 of the sleeve facilitating the installation upon the ejector tube E or larger diameter suction tube, as required.

Figure 4:
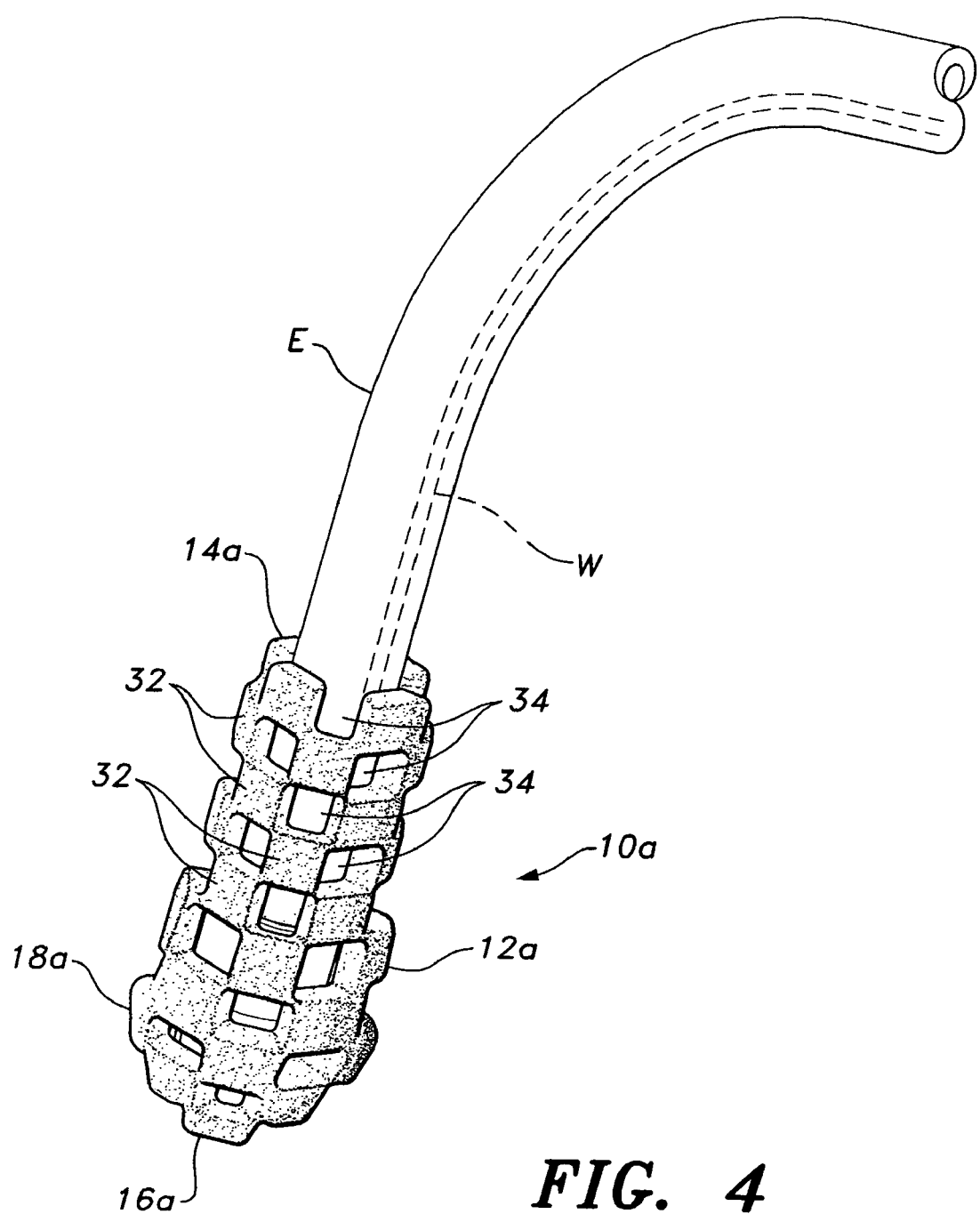
FIG. 4 is an environmental perspective view of an alternative embodiment of a protective sleeve for a saliva ejector according to the present invention installed upon an ejector tube, having alternating open and closed squares in a checkerboard pattern.

FIG. 4 of the drawings illustrates a protective sleeve 10a formed of an alternative material comprising a sheet of material having a regular geometric pattern of relatively small open and closed squares, respectively 32 and 34, with the squares joined to one another at their diagonal apices. The closed portions 32 thus define complementary open square areas 34 diagonally therebetween, the open areas 34 providing for the flow of saliva and/or other liquids therethrough when the ejector mechanism is in operation. It will be seen that the geometric pattern of alternating open and closed areas of the sleeve 10a may comprise any suitable geometric figures, e.g., triangles, etc., as desired. The sleeve 10a has a general configuration essentially the same as that of the sleeve 10 of FIGS. 1 through 3, i.e., having an elongate body 12a with an open tube installation end 14a and opposite closed distal end 16a, with a larger diameter externally bulbed distal end portion 18a. The internal passage, although not shown in FIG. 4, may have essentially the same configuration as the truncated conical section passage 20 of the sleeve 10, with the sleeve 10a further including a forward cavity and necked-down portion therein for positive attachment to the end of an ejector tube E, as in the sleeve 10 of FIGS. 1 through 3.

Figure 5:
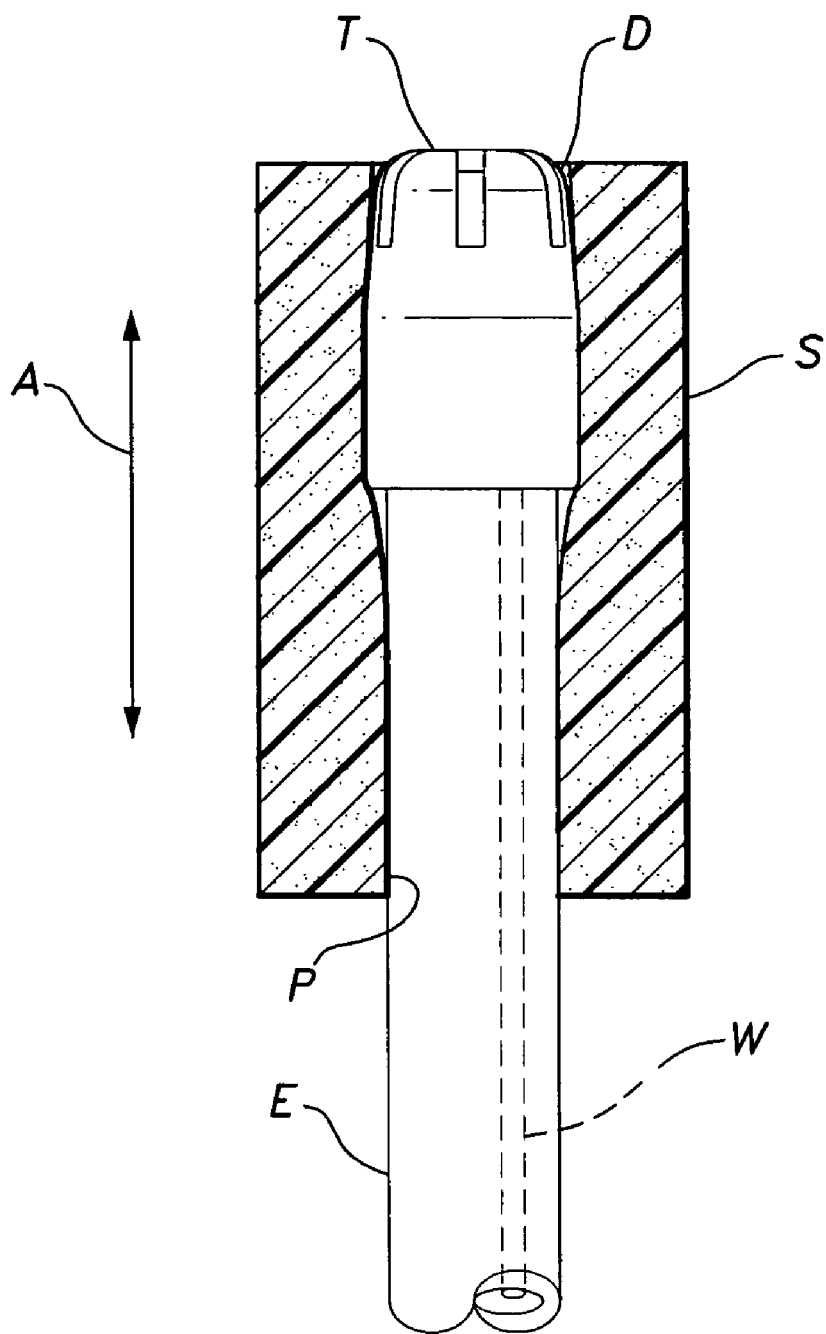
FIG. 5 is an environmental side elevation view in partial section showing a prior art protective sleeve for a saliva ejector having a continuous passage therethrough, shown installed upon a conventional ejector tube.

The prior art illustration of FIG. 5 shows a conventional sleeve S, with its open distal end D. Such conventional sleeves S are manufactured relatively cheaply, and are molded upon a cylindrical core of uniform diameter. As a result, such a conventional sleeve S is prone to slipping further down the length of the tube E beyond the distal tip T thereof, or, conversely, slipping over the tip T and falling from the tube E, generally as shown by the positional shift arrow A. This slippage is facilitated by the inherent lubricity of saliva, which seeps between the interstice between the constant diameter central inner passage P of the sleeve S and the wall of the ejector tube E contained therein. Slippage of the sleeve S in either direction requires the dentist or assistant to stop work to retrieve and/or reposition the sleeve S properly upon the ejector tube E. This may be required at least a few times in the course of a single dental procedure, which can add up to a significant amount of lost time during the course of a typical day.

It is to be understood that the present invention is not limited to the embodiments described above, but encompasses any and all embodiments within the scope of the following claims.

I claim:

1. A protective sleeve for a saliva ejector, the ejector having a tubular portion with a porous distal end portion of larger diameter than the tubular portion, the sleeve comprising a soft, resilient, porous body having a generally cylindrical external configuration with an open end and a closed end opposite the open end, the body further defining:

a frustoconical ejector tube passage disposed substantially concentrically therein, the ejector tube passage having a large diameter opening at the open end of the body and a small diameter neck portion disposed generally medially within the body; and a generally cylindrical cavity extending from the small diameter end of the ejector tube passage terminate near the closed end of the body, the cavity having an intermediate diameter smaller than the large diameter opening and greater than the small diameter neck portion of the ejector tube passage, the neck portion of the ejector tube passage forming a body retaining element when the body is installed upon the saliva ejector tube with the cavity snugly surrounding the end portion thereof;

a bulbed portion disposed externally upon the closed end of the body, the bulbed portion having a larger diameter than the body and being a relatively smaller extent than said cylindrical extent of said body; and a saliva ejector having a tubular portion with a porous distal end portion of larger diameter than the tubular portion thereof, whereby the generally cylindrical cavity snugly grips the distal end portion to provide positive elastic attachment of the sleeve to the ejector tube.

2. The protective sleeve for a saliva ejector according to claim 1, wherein the body is formed of open cell foam plastic material.

3. The protective sleeve for a saliva ejector according to claim 1, wherein the body is formed of a sheet of material having a regular geometric pattern of alternating open and closed areas.

4. The protective sleeve for a saliva ejector according to claim 3, wherein the regular geometric pattern comprises small squares joined to one another at their diagonal apices.

* * * * *